United States Patent [19]

Oshiro et al.

[11] Patent Number: 4,914,094
[45] Date of Patent: Apr. 3, 1990

[54] METHOD FOR TREATING HYPOXIA

[75] Inventors: Yasuo Oshiro; Masaaki Osaki; Tetsuro Kikuchi, all of Tokushima, Japan

[73] Assignee: Otsuka Pharmaceutical Co., Ltd., Japan

[21] Appl. No.: 326,845

[22] Filed: Mar. 21, 1989

Related U.S. Application Data

[63] Continuation of Ser. No. 938,068, Dec. 4, 1986, abandoned.

[30] Foreign Application Priority Data

Dec. 9, 1985 [JP] Japan .................................. 60-277632
Dec. 9, 1985 [JP] Japan .................................. 60-277633
Dec. 9, 1985 [JP] Japan .................................. 60-277634

[51] Int. Cl.$^4$ .............. A61K 31/55; A61K 31/54; A61K 31/535; A61K 31/50
[52] U.S. Cl. ............................ 514/213; 514/224.2; 514/230.5; 514/247; 514/299
[58] Field of Search ............ 514/213, 222, 233, 231.5, 514/247, 299, 253, 224.4; 540/523; 544/1, 336, 363; 546/112, 114, 115

[56] References Cited

U.S. PATENT DOCUMENTS 4,154,832   5/1979  Silvestrini ........................ 514/253
4,734,416   3/1988  Banno et al. ...................... 514/253

FOREIGN PATENT DOCUMENTS 55-124766   9/1980  Japan .
 56-49361   5/1981  Japan .
57-145872   9/1982  Japan .
57-193461  11/1982  Japan .
59-7067565  4/1984  Japan .

OTHER PUBLICATIONS

Tucker, Agents and Actions, vol. 10, No. 3, Jun. 1980, pp. 207–212.
Larsson et al., Acta Paediatrica Scandinavica, vol. 71, No. 3, May 1982, pp. 399–402.

Primary Examiner—John W. Rollins
Attorney, Agent, or Firm—Finnegan, Henderson, Farabow, Garrett & Dunner

[57] ABSTRACT

A method for curing and/or improving hypoxia characterized by administering a compound represented by the general formula (1),

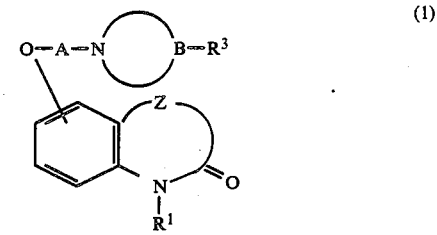

said compounds have been known in prior art literatures, for example, as carbostyril derivatives in Japanese Patent Kokai No. 54-160389 (1979), etc., as benzoxazine derivatives in Japanese Patent Kokai No. 59-70675 (1984), and as benzoazepine derivatives in Japanese Patent Kokai No. 57-193461 (1982), and they have been known as central nervous system controlling agents and antihistaminic agents.

The present invention was established on the basis of the findings that the compounds represented by the general formula (1) possess excellent pharmacological activities for curing and/or improving hypoxia and also possess excellent anti-oxidative activities, which could not have been anticipated from the disclosures in the prior art literatures.

15 Claims, No Drawings

METHOD FOR TREATING HYPOXIA

This is a continuation of application Ser. No. 938,068, filed Dec. 4, 1986, now abandoned.

FIELD OF THE INVENTION

The present invention relates to method for curing and/or improving hypoxia characterized by administerting a compound represented by the general formula (1),

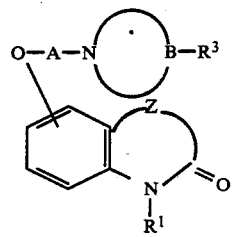

wherein $R^1$ is a hydrogen atom, a lower alkyl group, a lower alkenyl group, a lower alkynyl group or a phenyl-lower alkyl group; Z is a group of the formula

(wherein $R^2$ is a hydrogen atom or a lower alkyl group; and the bond being indicated as ⁻⁻⁻ is a single or double bond), or a group of the formula —(CH$_2$)$_3$—, —O—CH$_2$— or —S—CH$_2$—; $R^3$ is a pyridyl group, or a phenyl group which may have 1 to 3 substituents selected from the group consisting of a halogen atom, a lower alkyl group, a lower alkoxy group and a hydroxy group; and a group of the formula

represents a group of the formula

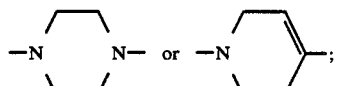

and A is a lower alkylene group; provided that when a group of the formula

is a group of the formula

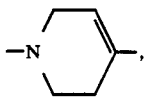

then Z is a group of the formula

and at the same time $R^3$ should be neither a pyridyl group nor a phenyl group having at least one hydroxy group as the substituent; or when $R^3$ is a pyridyl group, then Z is a group of the formula

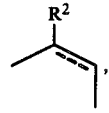

or a salt thereof.

PRIOR ART

Among compounds represented by the general formula (1), wherein Z is a group of the formula

(wherein $R^2$ is a hydrogen atom or a lower alkyl group; and the bond being indicated as ⁻ is a single or double bond) have already been known in prior art literatures, for example, Japanese Patent Application Kokai (Laid-open) Nos. 54-160389 (1979), 55-2693 (1980), 55-124766 (1980), 55-129268 (1980), 56-49359 (1981), 56-49361 (1981), 56-164186 (1981), 57-145872 (1982) and others. Additionally, among compounds represented by the general formula (1), wherein Z is a group of the formula —O—CH$_2$— or —S—CH$_2$— have already been known in prior art literatures, for example, Japanese Patent Application Kokai (Laid-open) No. 59-70675 (1984) and others. Furthermore, among compounds represented by the general formula (1), wherein Z is a group of the formula —(CH$_2$)$_3$— have already been known in prior art literatures, for example, Japanese Patent Application Kokai (Laid-Open) No. 57-193461 (1982) and others.

However, compounds represented by the general formula (1) known in these prior art literature are only disclosed as having central nervous system controlling activities and anti-histaminic activities.

BRIEF DESCRIPTION OF THE INVENTION

As the results obtained from extensive studies on the compounds represented by the general formula (1), the present inventors have found the facts that these compounds possess activites for improving hypoxia, said activities could not have been anticipated at all from the central nervous system controlling activities and anti-histaminic activities thereof being known in the prior art literatures. The present invention has estabilished on the basis of such new findings thereon.

An object of the present invention is to provide a method for curing and/or improving hypoxia characterized by administering a compound represented by the general formula (1).

Another object of the present invention is to provide a use of a compound represented by the general formula (1) for anti-oxidant.

DETAILED EXPLANATION OF THE INVENTION

Generally speaking, oxygen is an essential element to the living body for sustaining the life through release of energies and metabolisms. Oxygen is converted into so-called "active oxygen radicals", for example, oxygen anion radicals, peroxide ions, hydroxyl radicals, etc., in various biochemical reactions, such as energy releasing reactions, enzymatic reactions and other reactions caused by exposures of ultraviolet rays and various radiations.

The active oxygen radicals are indeed useful for the living body in the actions of oxygenase and of phagocytosis carried out by leucocytes. On the other hand, the active oxygen radicals promote peroxidation reaction of unsaturated fatty acids, such as oleic acid, linoleic acid, linolenic acid and arachidonic acid, etc., said unsaturated fatty acids are existing abundantly in the living body and are the main constituents of the biomembranes. the peroxidation of said unsaturated fatty acids produce peroxidized substances such as peroxidized lipids. Furthermore, similar to the above-mentioned active oxygen radicals, said peroxidized substance also produce alkoxy radicals and hydroxyl radicals which will attack the biomembranes and will result disorder of the biomembranes and deactivation of various useful enzymes working in the living body. [See, "TAISHA" (Metabolisms), Vol. 15, No. 10, (1978), The Special Issue on Active Oxygen.]

On the other hand, there are existing some other enzymes, such as superoxide dismutase (hereinafter referred to as "SOD"), catalase, glutathion peroxide, etc., in the living body. These enzymes prevent the deactivation of metabolisms from the attack caused by the active oxygen radicals. Additionally, there are existing several vitamins, such as tocopherols (vitamin E groups) having antioxidative activities in the living body.

Generally, the normal homeostasis mechanisms in the living body are sustained by the actions of these enzymes and vitamins having antioxidative activities. However, sometimes the prophylaxis mechanisms in the living body being suitably maintained by the actions of these enzymes and vitamins may be defected by certain reasons, and the formation of the active oxygen radicals in an amount exceeds the ability of the prophylaxis mechanisms in the living body, as well as the formation and accumulation of the peroxidized substances are observed.

In such cases, when the prophylaxis mechanisms in the living body are defected, then several severe disorders such as various diseases caused by the aggregation of the platelets, inflammations, disorders of the liver, arteriosclerosis, hemolysis, senescence or presbyopherenia, retinosis, disorder of the lungs, disorders of the heart and the lungs caused by the actions of certain drugs, ischematic coronary heat disease and the like will be occurred by accompanying with the progressive chain reactions of the peroxidation.

Hitherto, compounds having actions for scavenging the active oxygen radicals which are considered to be the main factors of the above-mentioned various diseases, and for preventing or lowering the formation and accumulation of the peroxidized substances in the living body were known and called them as antioxidants. A number of studies of prophylaxis and curative effects by using these antioxidants have been reported in several literatures.

As to enzymatic preparations containing SOD and other enzymes as mentioned previously are reported in "SUPEROXIDE-TO-IGAKU" (Superoxide and Medicines) by Yoshihiko Ohyanagi, pages 137 to 141, published from Kyoritsu Publishing Co., Ltd.; "SAISHIN-NO-IGAKU" (Modern Medicine)-Special Issue of active Oxygen and Its Medicinal Roles, Vol. 39, No. 7, (1984); "ENSHOH" (Inflammations), Vol. 1, page 699, (1981); Ibid., Vol. 2, page 367, (1982); Current Therp. Rep., Vol. 20, pages 62 to 69, (1976); "Perspective in Inflammation", published from Red-Wood Burn Ltd., pages 527 to 544, (1977); Acta. Physiol. Scand., Vol. 49, No. 2, Suppl. pages 59 to 65, (1980); Proc. Nat. Acad. Sci., U.S.A., Vol. 79, pages 7509 to 7513, (1982); "Pathology of Oxygen" published from Academy Press, Inc., pages 85 to 97, (1982); J. Clinic. Invest., Vol. 67, page 983, (1981); Ibid., Vol. 70, pages 650 to 658, (1982); "Pathology of Oxygen" published from Academy Press, Inc., pages 261 to 275, (1982); Biochem. Biophys. Acta, Vol. 542, pages 28 to 38, (1978); Bull. European Physiopathol. Resp., Vol. 17, Suppl. pages 287 to 288, (1981); "Pathology of Oxygen" published from Academy Press, Inc., pages 277 to 302, (1982);, Reports on Studies of Behcet's Disease, issued from specified Intractable Disease Research Group, Ministry of Public Health and Welfare, the Japanese Government (1982–1983); J. Immunol., Vol. 128, page 2770, (1982); articles of butylhydroxytoluene (BHT), butylhydroxyanisole (BHA), -tocopherol (vitamin E) and others, reported by Makoto Mino and Hidetaka Tanaka, "IYAKU-JOURNAL" (Pharmaceutical Journal), Vol, 19, No. 12, pages 2351 to 2359, (1983); by Toshihiko Suematsu, Ibid., Vol. 19, No. 5, pages 909 to 914, (1983); Arch. Biochem. Biophys., Vol., 227, pages 534 to 541, (1976); Adv. Cancer Res., Vol. 26, page 197, (1978) and others.

Compounds represented by the general formula (1) according to the present invention possess excellent activities for improving anoxemic and hypoxic symptoms and syndromes accompanied therewith. More particularly, compounds represented by the general formula (1) and salt thereof are useful as for example, cerabral activators, curative and/or improving agents for cerebral blood vessel disturbance (such as cerebral hemorrhage, cerebral infaraction, subarachnoidal hemorrhage, hypertensive encephalopathy, etc.), agents for improving disturbance of consciousness caused by encephalitis, cerebral tumor, head injuries, metabolism disturbances, chemical poisonings and physical insuries, curative and/or improving agents for prognostic symptoms caused by the above-mentioned diseases, curative and/or improving agents for depression of attention, hyperanakinesia, speech disturbance and mental retardation, curative agent for amnesia, curative agent for presbyophrenia, agent for respiratory arrest caused by poisoning with potassium cyanide, improving agent for hypoxia, preventive agent for arrhythmia caused by the shortage of oxygen and heart failure, and others.

Additionally, compounds represented by the general formula (1) and salts thereof according to the present invention possess actions for scavenging active oxygen radicals and for preventing and lowering the formation of peroxidized lipids in the living body. Therefore, compounds of the general formula (1) and salts thereof are useful as prophylactic and treating agents for various disturbances and diseases caused by the excessive formation of the above-mentioned active oxygen radicals, the accumulation of peroxidized lipids in the living body or for deficiencies of protective mechanisms in the living body against such active oxygen radicals and peroxidized lipids. Thus, compounds of the general formula (1) and salts thereof according to the present invention are useful as antiarterioscalerosis agents, anti-inflammatory agents, analgesics, treating agents for autoimmune diseases, inhibitory agents for aggregation of platelets, hypotensive agents, anti-hyperlipemia agents, prophylactic and treating agents for retinosis of immature infant and for cataract and the like.

Furthermore, compounds of the general formula (1) and salts thereof according to the present invention are useful as anti-oxidative agents for oils and fats contained in various processed food products.

In the present specification, the symbols of $R^1$, $R^2$, $R^3$ and A are exemplified more specifically as follows.

As to the lower alkyl group, a straight- or branched-chain alkyl group having 1 to 6 carbon atoms, such as methyl, ethyl, propyl, isopropyl, butyl, tert-butyl, pentyl, hexyl groups and the like can be exemplified.

As to the lower alkenyl group, a straight- or branched-chain alkenyl group having 2 to 6 carbon atoms, such as vinyl, allyl, 2-butenyl, 3-butenyl, 1-methylallyl, 2-pentenyl, 2-hexenyl groups and the like can be exemplified.

As to the lower alkenyl group, a straight- or branched-chain alkenyl group having 2 to 6 carbon atoms, such as ethynyl, 2-propynyl, 2-butynyl, 3-butynyl, 1-methyl-2-propynyl, 2-pentynyl, 2-hexynyl groups and the like can be exemplified.

As to the phenyl-lower alkyl group, a phenylalkyl group in which the alkyl moiety is a straight- or branched-chain alkylene group having 1 to 6 carbon atoms, such as benzyl, 2-phenylethyl, 1-phenylethyl, 3-phenylpropyl, 4-phenylbutyl, 1,1-dimethyl-2-phenylethyl, 5-phenylpentyl, 6-phenylhexyl, 2-methyl-3-phenylpropyl group or the like can be exemplified.

As to the halogen atoms, a fluorine, chlorine, bromine and iodine atoms can be exemplified.

As to the lower alkoxy group, a straight- or branched-chain alkoxy group having 1 to 6 carbon atoms, such as methoxy, ethoxy, propoxy, isopropoxy, butoxy, tert-butoxy, pentyloxy, hexyloxy groups and the like can be exemplified.

As to the phenyl group which may have 1 to 3 substituents selected from the group consisting of a halogen atom, a lower alkyl group, a lower alkoxy group and a hydroxyl group, a phenyl group which may have 1 to 3 substituents on the phenyl ring, selected from the group consisting of a halogen atom, a straight- or branched-chain alkyl group having 1 to 6 carbon atoms, a straight- or branched-chain alkoxy group having 1 to 6 carbon atoms and a hydroxyl group, such as phenyl, 2-chlorophenyl, 3-chlorophenyl, 4-chlorophenyl, 2-fluorophenyl, 3-fluorophenyl, 4-fluorophenyl, 2-bromophenyl, 3-bromophenyl, 4-bromophenyl, 2-iodophenyl, 4-iodophenyl, 3,5-dichlorophenyl, 2,6-dichlorophenyl, 3,4-dichlorophenyl, 3,4-difluorophenyl, 3,5-dibromophenyl, 3,4,5-trichlorophenyl, 2-methylphenyl, 3-methylphenyl, 4-methylphenyl, 2-ethylphenyl, 3-ethylphenyl, 4-ethylphenyl, 3-isopropylphenyl, 4-hexylphenyl, 3,4-dimethylphenyl, 2,5-dimethylphenyl, 2,3-dimethylphenyl, 3,4,5-trimethylphenyl, 2-methoxyphenyl, 3-methoxyphenyl, 4-methoxyphenyl, 2-ethoxyphenyl, 3-ethoxyphenyl, 4-ethoxyphenyl, 4-isopropoxyphenyl, 4-hexyloxyphenyl, 3,4-dimethoxyphenyl, 3,4-diethoxyphenyl, 2,5-dimethhoxyphenyl, 3,4,5-trimethoxyphenyl, 3-methyl-4-chlorophenyl, 2-chloro-6-methylphenyl, 2-methoxy-3-chlorophenyl, 2-hydroxyphenyl, 3-hydroxyphenyl, 3,4-dihydroxyphenyl groups and the like can be exemplified.

As to the lower alkylene group, a straight- or branched-chain alkylene group having 1 to 6 carbon atoms, such as methylene, ethylene, trimethylene, 2-methyltrimethylene, 2,2-dimethyltrimethylene, 1-methyltrimethylene, methylmethylene, ethylmethylene, tetramethylene, pentamethylene, hexamethylene groups and the like can be exemplified.

Compounds represented by the general formula (1) according to the present invention can be prepared by various methods, and preferable method is shown by the reaction formula as follows.

Reaction formula

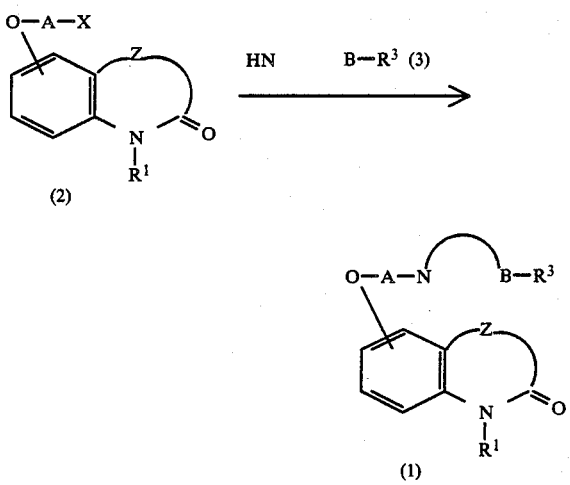

wherein $R^1$, $R^3$, A, Z and a group of the formula

are the same as defined above; and X is a halogen atom, a lower alkanesulfonyloxy group, an arylsulfonyloxy group or an aralkylsulfonyloxy group.

A compound (1) can be prepared by reacting a compound (2) with a compound (3).

Both compounds (2) and (3) to be used as the starting materials are known compounds. As to the lower alkanesulfonyloxy group defined in the symbol X in the general formula (2), it can specifically be exemplified as methanesulfonyloxy, ethanesulfonyloxy, isopropanesulfonyloxy, propanesulfonyloxy, butanesulfonyloxy, tert-butanesulfonyloxy, pentanesulfonyloxy and hexanesulfonyloxy groups, etc. As to the arylsulfonyloxy group defined in the symbol X in the general formula (2), it can specifically be exemplified as a substituted- or un-substituted-arylsulfonyloxy group, such as phenylsulfonyloxy, 4-methylphenylsulfonyloxy, 2-methylsulfonyloxy, 4-nitrophenylsulfonyloxy, 4-methoxyphenylsulfonyloxy, 3-chlorophenylsulfonyloxy and α-naphthylsulfonyloxy groups, etc. Furthermore, as to the aralkylsulfonyloxy group defined in the symbol X in the general formula, it can specifically be exemplified as a substituted- or unsubstituted-aralkylsulfonyloxy group, such as benzylsulfonylooxy, 2-phenylethylsulfonyloxy, 4-phenylbutylsulfonyloxy, 4-methylbenzylsulfonyloxy, 2-methylbenzylsulfonyloxy, 4-nitrobenzylsulfonyloxy, 4-methoxybenzylsulfonyloxy, 3-chlorobenzylsulfonyloxy and α-napthylmethylsulfonyloxy groups, etc.

The reaction of a compound of the general formula (2) with a compound of the general formula (3) can be carried out in the absence or generally in the presence of an inert solvent, at room temperature to 200° C., preferably at 60° to 120° C., and the reaction is completed within about a several hours to 24 hours. As to the inert solvent used in the reaction, ethers such as dioxane, tetrahydrofuran, ethylene glycol, dimethyl ether, etc.; aromatic hydrocarbons such as benzene, toluene, xylene, etc.; lower alcohols such as methanol, ethanol, isopropanol, etc.; and polar solvents such as dimethylformamide, dimethyl sulfoxide, acetone, acetonitrile, N-methylpyrrolidone, hexamethylphosphoric triamide, etc. can be used.

The above-mentioned reaction can be carried out advantageously by using a basic compound as deacidifying agent. As to the basic compound, it can be exemplified potassium carbonate, sodium carbonate, sodium hydroxide, sodium hydrogen carbonate, sodium amide, sodium hydride, 1,8-diazabicyclo[5,4,0]-7-undecene, tertiary amines such as triethylamine, tripropylamine, pyridine, and quinoline, etc.

The above-mentioned reaction can also be carried out if necessary by adding with an alkali metal iodide, such as potassium iodide, sodium iodide, etc.

The ratio of the amount of a compound of the general formula (2) to the amount of a compound of the general formula (3) is generally an equimolar quantity to a excess molar quantity of the latter to the molar quantity of the former, preferably an equimolar quqntity to 5 times the molar quantity, more preferably, 1 to 1.2 times the molar quantity of the latter can be used.

Thus obtained compounds represented by the general formula (1) can be separated and purified by usual separation means, for example solvent extraction, dilution, recrylstallization, column chromatography, preparative thin-layer chromatography and the like.

Compounds of the above-mentioned general formula (1) according to the present invention including inevitably their stereo isomers and optical isomers.

Compounds of the above-mentioned general formula (1) according to the present invention can easily be converted into their acid-addition salts by reacting with pharmaceutically acceptable acids, and the present invention also including said acid-addition salts. As to the pharmaceutically acceptable acids, examples are inorganic acids such as hydrochloric acid, sulfuric acid, phosphoric acid, and hydrobromic acid, etc.; organic acids such as acetic acid, oxalic acid, succinic acid, maleic acid, fumaric acid, malic acid, tartaric acid, citric acid, malonic acid, methanesulfonic acid, benzoic acid, etc. are included.

Compounds of the above-mentioned general formula (1) according to the present invention can be used in any form of usual preparations of pharmaceutical compositions together with usual pharmaceutically acceptable carriers. Examples of pharmaceutically acceptable carriers which are selected depend on the desired form of pharmaceutical compositions, including diluents and excipients such as fillers, diluents, binders, wetting agents, disintegrating agents, surface active agents, lublicants, etc. No particular restriction is made to the administration unit forms and the pharmaceutical compositions can be selected from any desired unit form including tablets, pills, powders, liquors, suspensions, emulsions, granules, capsules, suppositories, injection preparations (including solutions, suspensions, etc.) ointments, etc.

For the purpose of to make in the form of tablets, carriers which are widely used in this field can be used, for example, excipients such as lactose, sucrose, sodium chloride, glucose, urea, starch, calcium carbonate, kaolin, crystalline cellulose, silicic acid, etc.; binding agents such as water, ethanol, propanol, simple sirup, glucose solution, starch solution, gelatin solution, carboxymethyl cellulose, shelac, methyl cellulose, potassium phosphate, polyvinylpyrrolidone, etc.; disintegrating agents such as dried starch, sodium alginate, agar-agar powder, laminalia powder, sodium hydrogen carbonate, calcium carbonate, esters of polyoxyethylene sorbitan fatty acids, sodium laurylsulfate, monoglyceride of stearic acid, starch lactose, etc.; disintegration inhibitors such as sucrose, stearin, coconut butter, hydrogenated vegetable oils, etc.; absorption accelarators such as quanternary ammonium bases, sodium laurylsulfonate, etc.; wetting agents such as glycerin, starch, etc.; adsorbing agents such as starch, lactose, kaolin, bentonite, colloidal silicic acid, etc.; and lubricants such as purified talc, stearic acid salts, boric acid powder, polyethylene glycols, etc. If necessary, the tablets can be further coated with usual coating materials to make them into coated tablets, for example tablets coated with sugar, tablets caoted with gelatin film, tablets coated with enteric coating layers, tablets coated with films or double layer tablets as well as multiple layer tablets, etc.

For the purpose of to make in the form of pills, any carrier which is known and used widely in this field can be used, for example, excipients such as glucose, lactose, starch, coconut butter, hydrogenated vegetable oils, kaolin, talc, etc.; binders such as powdered gum arabic, powdered tragacanth gum, gelatin, ethanol, etc.; disintegrating agents such as laminaria, agar-agar, etc.

For the purpose of to make in the form of suppositories, carriers which are known and widely used in this field can also be used, for example, polyethylene glycols, coconut butter, higher alcohols, esters of higher alcohols, gelatin, semi-synthesized glycerides, etc.

For the purpose of to make in the form of injection preparations, solutions and suspensions prepared are further sterilized and are preferably isotonic to the blood. In preparing injection preparations in the form of solutions, emulsions and suspensions, any carrier which is known and is widely used in this field can also be used, for example water, ethyl alcohol, prpylene glycol, ethoxylated isostearyl alcohol, polyoxyated isostearyl alcohol, polyoxyethylene sorbitan fatty acid esters, etc. In these instances, adequate amounts of sodium chloride, glucose or glycerin may be added to make the desired injection preparations isotonic. Furthermore, usual dissolving agents, buffer solutions, analgesic agents may be added. Also coloring materials, preservitives, perfumes, seasoning agents, sweetening agents and other medicines may be added in the desired pharmaceutical preparations, if necessary.

For the purpose of to make the preparation in the form of pastes, creams and gels, diluents which are known and widely used in these fields can be also used, for example white petrolatum, paraffin, glycerin, cellulose derivatives, polyethylene glycols, silicones, bentonite, etc.

The amount of compound represented by the general formula (1) or salt thereof to be contained in the pharmaceutical composition according to the present invention is not specifically restricted, and can suitably be selected from a wide range, and generally 1 to 70% by weight of the compound or salt thereof may be contained in the pharmaceutical composition.

Methods for administering the above-mentioned pharmaceutical composition are not specifically restricted, thus, the compositions can be administered in various forms of pharmaceutical preparations depend on the age, the distinction of sex, the degree of symptoms and other conditions of the patiant without any restriction. For example, tablets, pills, solutions, suspensions, emulsions, granules and capsules are administered orally; injection preparations are administered intraveneously singly, or administered with usual injectable transfusions such as glucose solutions, amino acids solutions, etc.; if necessary, the injection preparations are administered singly intramuscularly, intracutaneously, subcutaneously or intraperitoneally; and the suppositories are administered into rectum.

The dosage of the above-mentioned pharmaceutical compositions can be selected suitably according to the methods for administrations, the age of the patiant, the distinction of sex and other conditions as well as the degree of the symptoms, and generally 0.2 to 200 mg/kg/day of compound represented by the general formula (1) or salt thereof may be used.

Reference Example 1

2.0 Grams of 7-(3-chloropropoxy)-3,4-dihydrocarbostyril and 1.6 g of sodium iodide were admixed with 60 ml of acetone, and the mixture thus obtained was stirred at 40° to 50° C. for 2 hours. Then to this reaction mixture was added 60 ml of dimethylformamide, next acetone was removed by evaporation under reduced pressure, and 1.74 g of 4-(3-methylphenyl)-1,2,5,6-tetrahydropyridine and 2 ml of triethylamine were added thereto, further the whole mixture was stirred at 50° to 60° C. for 6 hours. This reaction mixture was concentrated under reduced pressure, and to the residue thus obtained was added 80 ml of 5%-sodium hydrogen carbonate aqueous solution and stirred so as to crystallize the organic substance in the mixture. The precipitate was collected by filtration, washed with water, and dried. Recrystallized from ethanol-water to yield 1.8 g of 7-{3-[4-(3-methylphenyl)-1,2,5,6-tetrahydro-1-pyridyl]-propoxy}-3,4-dihydrocarbostyril. Colorless flake-like crystals. Melting point: 143°-145° C.

Reference Example 2

4.8 Grams of 7-(3-chloropropoxy)-3,4-dihydrocarbstyril and 3.5 g of sodium iodide were admixed with 50 ml of acetone, and the mixture thus obtained was refluxed for 3 hours. Then to this reaction mixture was added 40 ml of dimethylformamide, next acetone was removed by evaporation under reduced pressure, and 3.9 g of 4-(4-methylphenyl)-piperazine and 3.0 g of triethylamine were added thereto, further the whole mixture was stirred at 70° to 80° C. for 7 hours. After removal of the solvent by evaporation under reduced pressure, 60 ml of 5%-sodium hydrogen carbonate aqueous solution was added to the resulting residue. Then this mixture was extracted with chloroform, and the chloroform layer was wahsed with water twice, dried then the solvent was removed by evaporation to obtain the residue. Recrystallized from ethanol to obtain 6.0 g of 7-{3-[4-(4-methylphenyl)-1-piperazinyl]-propoxy}-3,4-dihydrocarbostyril. Yellow needle-like crystals. Melting point: 149°-150° C.

By using suitable starting materials and by methods similar to that described in the above-mentioned Reference Example 2, there were prepared compounds as follows:

7-{3-[4-(3-Chlorophenyl)-1-piperazinyl]propoxy}-3,4-dihydrocarbostyril

Colorless needle-like crystals (recrystallized from ethanol. Melting point: 156°-158° C.

7-{3-[4-(4-Chlorophenyl)-1-piperazinyl]propoxy}-3,4-dihydrocarbostyril

Light yellow prism-like crystals (recrystallized from ethanol). Melting point: 200°-202° C.

7-{3-[4-(3-Methoxyphenyl)-1-pieprazinyl]propoxy}-3,4-dihydrocarbostyril

Colorless needle-like crystals (recrystallized from ethanol). Melting point: 142°-143° C.

Pharmacological Test (Survival test under hypoxic condition)

This test was conducted by procedures similar to those described in an article reported in "Arch. Int. Pharmacodyn., Vol. 233, page 137, (1978)".

ICR-strain male mice (weighing 20 to 30 g) were used as the test animals. Four mice were used as one test group, the mice were placed in a glass desciccator with which a stop valve was equipped. Inside pressure of the desciccator was reduced until 180 mm-Hg by sucking the air by using a vacuum pump, then the stop valve was closed.

Survival time of each of the test mice was determined as a length of time between the beginning of the vacuum pump operation and the arrest of breathing of the mouse.

Each of the test compounds was orally administered to the mouse at 15 minutes before the beginning of the vacuum pump operation.

The survival time of the mouse of the reference group was referred to as 100, and the ratio of the survival time of the mouse of the test group was calculated by the following formula and obtained the survival ratio (%):

$$\text{Survival ratio (\%)} = \frac{\left[\begin{array}{c}\text{Survival time of the mouse administered with test compound}\end{array}\right]}{\left[\begin{array}{c}\text{Survival time of the mouse of the reference group}\end{array}\right]} \times 100$$

The test results are shown in Table 1 below.
Test Compound Nos.
1. 7-{3-[4-(3-Methylphenyl)-1-piperazinyl]propoxy}-3,4-dihydrocarbostyril
2. 7-{3-[4-(4-Methylphenyl)-1-piperazinyl]propoxy}-3,4-dihydrocarbostyril
3. 7-{3-[4-(2,3-Dimethylphenyl)-1-piperazinyl]propoxy}carbostyril
4. 7-{3-[4-(3,4-Dimethylphenyl)-1-piperazinyl]propoxy}-3,4-dihydrocarbostyril
5. 7-{3-[4-(3-Chloro-4-methylphenyl)-1-piperazinyl]propoxy}-3,4-dihydrocarbostyril
6. 7-{3-[4-(3-chlorophenyl)-1-piperazinyl]propoxy}-3,4-dihydrocarbostyril
7. 7-{3-[4-(3-Chlorophenyl)-1-piperazinyl]propoxy}carbostyril
8. 7-{3-[4-(4-Chlorophenyl)-1-piperazinyl]propoxy}-3,4-dihydrocarbostyril 9. 7-{3-[4-(3-Hydroxyphenyl)-1-piperazinyl]propoxy}-3,4-dihydrocarbostyril
10. 7-{3-[4-(4-Hydroxyphenyl)-1-piperazinyl]propoxy}-3,4-dihydrocarbostyril
11. 7-{3-[4-(3-Methylphenyl)-1,2,5,6-tetrahydro-1-pyridyl]propoxy}-3,4-dihydrocarbostyril
12. 7-{3-[4-(2,3-Dimethylphenyl)-1-piperazinyl]propoxy}-3,4-dihydrocarbostyril
13. 7-{3-[4-(Pyridyl-2-yl)-1-piperazinyl]propoxy}-3,4-dihydrocarbostyril
14. 5-{3-[4-(3-Methylphenyl)-1-piperazinyl]propoxy}-3,4-dihydrocarbostyril
15. 7-{3-[4-(4-Methylphenyl)-1,2,5,6-tetrahydro-1-pyridyl]propoxy}-3,4-dihydrocarbostyril
16. 6-{3-[4-(3-Methylphenyl)-1-piperazinyl]propoxy}-2H-1,4-benzoxazin-3(4H)-one
17. 6-{3-[4-(3-Methylphenyl)-1-piperazinyl]propoxy}-2H-1,4-benzothiazin-3(4H)-one
18. 8-{3-[4-(3-Methylphenyl)-1-piperazinyl]propoxy}-2H-1,4-benzoxazin-3(4H)-one
19. 6-[3-(4-Phenyl-1-piperazinyl)propoxy]-2H-1,4-benzoxazin-3(4H)-one
20. 6-{3-[4-(2,3-Dimethylphenyl)-1-pieprazinyl]propoxy}-2H-1,4-benzoxazin-3(4H)-one
21. 8-{3-[4-(3-Methylphenyl)-1-piperazinyl]propoxy}-2,3,4,5-tetrahydro-1H-1-benzoazepin-2-one
22. 8-{3-[4-(3-Chlorophenyl)-1-piperazinyl]propoxy}-2,3,4,5-tetrahydro-1H-1-benzoazepin-2-one
23. 1-methyl-7-{3-[4-(3-Chlorophenyl)-1-piperazinyl]propoxy}-3,4-dihydrocarbostyril
24. 7-{3-[4-(3-Methoxyphenyl)-1-piperazinyl]propoxy}-3,4-dihydrocarbostyril
25. Chloropromazine [2-Chloro-N,N-dimethyl-10H-phenothiazine-10-propamine] - Reference compound

TABLE 1

| Test compound No. | Dosage (mg/kg, p.o.) | Survival ratio (%) |
|---|---|---|
| 1 | 30 | 360 |
| 2 | 30 | 675 |
| 3 | 30 | 511 |
| 4 | 30 | 579 |
| 5 | 30 | 162 |
| 6 | 30 | 723 |
| 7 | 30 | 377 |
| 8 | 30 | 746 |
| 9 | 30 | 119 |
| 10 | 30 | 118 |
| 11 | 30 | 647 |
| 12 | 30 | 394 |
| 13 | 30 | 243 |
| 14 | 30 | 237 |
| 15 | 30 | 128 |
| 16 | 30 | 927 |
| 17 | 30 | 197 |
| 18 | 30 | 258 |
| 19 | 30 | 135 |
| 20 | 30 | 649 |
| 21 | 30 | 395 |
| 22 | 30 | 164 |
| 23 | 100 | 280 |
| 24 | 30 | 407 |
| 25 | 30 | 53 |

Example of injection preparation - 1

| | |
|---|---|
| 7-{3-[4-(4-Methylphenyl)-1-piperazinyl]propoxy}-3,4-dihydrocarbostyril | 200 mg |
| Glucose | 250 mg |
| Distilled water for injection | q.s. |
| | 5 mg |

7-{3-[4-(4-Methylphenyl)-1-piperazinyl]propoxy}-3,4-dihydrocarbostyril and glucose were dissolved in distilled water for injection, the solution was filled in an ampule of 5 ml volume. After the air in the filled ampule was replaced with nitrogen gas, the ampule was sterilized with steam under pressure at 121° C. for 15 minutes to obtain the injection preparation having the above-mentioned formulation.

Example of injection preparation - 2

| | |
|---|---|
| 6-{3-[4-(3-Methylphenyl)-1-piperazinyl]propoxy}-2H-1,4-benzoxazin-3(4H)-one | 200 mg |
| Glucose | 250 mg |
| Distilled water for injection | q.s. |
| | 5 ml |

By a method similar to the above-mentioned Example of injection preparation - 1, the injection preparation having the above-mentioned formulation was obtained.

Example of injection preparation - 3

| | |
|---|---|
| 8-{3-[4-(3-Methylphenyl)-1-piperazinyl]propoxy}-2,3,4,5-tetrahydro-1H-1-benzoazepin-2-one | 200 mg |
| Glucose | 250 mg |
| Distilled water for injection | q.s. |
| | 5 ml |

By a method similar to that described in Example of injection preparation - 1, the injection preparation having the above-mentioned formulation was obtained.

Example of film coated tablets preparation - 1

| | |
|---|---|
| 7-{3-[4-(3-Chlorophenyl)-1-piperazinyl]propoxy}-3,4-dihydrocarbostyril | 100 g |
| Avicel (a trademark for microcrystalline cellulose, manufactured by Asahi Chemical Industry Co., Ltd.) | 40 g |
| Corn starch | 30 g |
| Magnesium stearate | 2 g |
| TC-5 (a trademark for hydroxypropyl methylcellulose, manufactured by The Shin-Etsu Chemical Co., Ltd.) | 10 g |
| Polyethylene glycol-6000 | 3 g |
| Castor oil | 40 g |
| Methanol | 40 g |

7-{3-[4-(3-Chlorophenyl)-1-piperazinyl]propoxy}-3,4-dihydrocarbostyril, Avicel, corn starch and magnesium stearate were admixed together and ground, then the mixture obtained was shaped into tablets by using a tablet machine (having 10 mm in diameter). The tablets obtained were coated with a film coating consisting of TC-5, polyethylene glycol-6000, castor oil and methanol to prepare the film coated tablets having the above-mentioned formulation.

Example of film coated tablets preparation - 2

| | |
|---|---|
| 6-{3-[4-(2,3-Dimethylphenyl)-1-piperazinyl]propoxy}-2H-1,4-benzoazin-3(4H)-one | 100 g |
| Avicel | 40 g |
| Corn starch | 30 g |
| Magnesium stearate | 2 g |
| TC-5 | 10 g |
| Polyethyle glycol-6000 | 3 g |
| Castor oil | 40 g |
| Methanol | 40 g |

Example of film coated tablets preparation - 3

| | |
|---|---|
| 8-{3-[4-(3-Chlorophenyl)-1-piperazinyl]-propoxy}-2,3,4,5-tetrahydro-1H-1-benzoazepin-2-one | 100 g |
| Avicel | 40 g |
| Corn starch | 30 g |
| Magnesium stearate | 2 g |
| TC-5 | 10 g |
| Polyethylene glycol-6000 | 3 g |
| Castor oil | 40 g |
| Methanol | 40 g |

By a method similar to that described in Example of film coated tablets preparation - 1, there were prepared film coated tablets having the above-mentioned formulation.

Example of ointment preparation - 1

| | |
|---|---|
| 7-{3-[4-(4-Chlorophenyl)-1-piperazinyl]-propoxy}-3,4-dihydrocarbostyril | 2 g |
| Purified lanolin | 5 g |
| White bees wax | 5 g |
| White petrolatum | 88 g |
| | 100 g |

White bees wax was warmed to make it in a liquid state, then 7-{3-[4-(4-chlorophenyl)-1-piperazinyl]-propoxy}-3,4-dihydrocarbostyril, purified lanolin and white petrolatum were added thereto. The mixture was warmed to make it in a liquid state, then stirred until solidified to prepare the ointment having the above-mentioned formulation.

Example of ointment preparation - 2

| | |
|---|---|
| 6-{3-[4-(3-Methylphenyl)-1-piperazinyl]-propoxy}-2H-1,4-benzoazin-3(4H)-one | 2 g |
| Purified lanoline | 5 g |
| White bees wax | 5 g |
| White petrolatum | 88 g |

By a method similar to that described in Example of ointment preparation - 1, there was prepared the ointment preparation having the above-mentioned formulation.

Example of ointment preparation - 3

| | |
|---|---|
| 8-{3-[4-(3-Methylphenyl)-1-piperazinyl]propoxy}-2,3,4,5-tetrahydro-1H-benzoazepin-2-one | 2 g |
| Purified lanoline | 5 g |
| White bees wax | 5 g |
| White petrolatum | 88 g |

By a method similar to that described in Example of ointment preparation - 1, there was prepared the ointment preparation having the above-mentioned formulation.

What is claimed is:

1. A method for treating hypoxia comprising, administering to a host in need of said treatment a compound or salt thereof represented by formula (1),

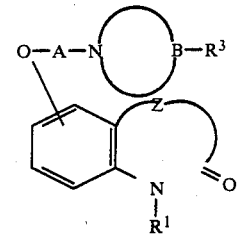

(1)

wherein $R^1$ is a hydrogen atom, a lower alkyl group, a lower alkenyl group, a lower alkynyl group or a phenyl-lower alkyl group; Z is a group of the formula

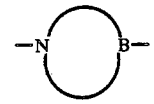

in which $R^2$ is a hydrogen atom or a lower alkyl group; and the bond indicated as ⹀ is a single or double bond, a group of the formula —(CH$_2$)$_3$—, a group of the formula —O—CH$_2$— or a group of the formula —S—CH$_2$—; $R^3$ is a pyridyl group, or a phenyl group which may have 1 to 3 substituents selected from the group consisting of a halogen atom, a lower alkyl group, a lower alkoxy group and a hydroxy group; and a group of the formula

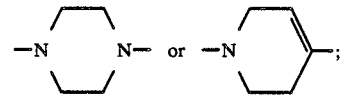

is a group of the formula

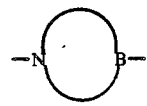

and A is a lower alkylene group; provided that when a group of the formula

is a group of the formula

then Z is a group of the formula

and at the same time $R^3$ should be neither a pyridyl group nor a phenyl group having at least one hydroxy group as the substituent; or when R³ is a pyridyl group, then Z is a group of the formula

2. The method according to claim 1, wherein R³ in the general formula (1) is a phenyl group which may have 1 to 3 substituents selected from the group consisting of a halogen atom, a $C_1$–$C_6$ alkyl group, a $C_1$–$C_6$ alkoxy group and a hydroxy group.

3. The method according to claim 2, wherein R³ in the general formula (1) is a phenyl group which may have 1 to 2 substituents selected from the group consisting of a halogen atom, a $C_1$–$C_6$ alkyl group, a $C_1$–$C_6$ alkoxy group and a hydroxy group.

4. The method according to claim 3, wherein Z in the general formula (1) is a group of the formula

(wherein R² is a hydrogen atom or a $C_1$–$C_6$ alkyl group; and the bond indicated as      is the same defined above).

5. The method according to claim 4, wherein R² in the general formula (1) is a hydrogen atom.

6. The method according to claim 3, wherein Z in the general formula (1) is a group of the formula —O—CH₂—.

7. The method according to claim 3, wherein Z in the general formula (1) is a group of the formula —(CH₂)₃— or a group of the formula —S—CH₂—.

8. The method according to claims 5, 6 or 7, wherein R¹ in the general formula (1) is a hydrogen atom or a $C_1$–$C_6$ alkyl group.

9. The method according to claim 1, wherein R³ in the general formula (1) is a pyridyl group.

10. A method for treating hypoxia which comprises administering to a host in need thereof a 7-{3-[4-(4-Methylphenyl)-1-piperazinyl]propoxy}-3,4-dihydrocarbostyril or a salt thereof in an amount effective for said treatment.

11. A method for treating hypoxia which comprises administering to a host in need thereof a 6-{3-[4-(3-(Methylphenyl)-1-piperazinyl]propoxy}-2H-1,4-benzoxazin-3(4H)-one or a salt thereof in an amount effective for said treatment.

12. A method for treating hypoxia which comprises administering to a host in need thereof a 7-{3-[4-(3-Chlorophenyl)-1-piperazinyl]propoxy}-3,4-dihydrocarbostyril or a salt thereof in an amount effective for said treatment.

13. A method for treating hypoxia which comprises administering to a host in need thereof a 7-{3-[4-(3-Methylphenyl)-1,2,5,6-tetrahydro-1-pyridyl]propoxy}-3,4-dihydrocarbostyril or a salt thereof in an amount effective for said treatment.

14. A method for treating hypoxia which comprises administering to a host in need thereof a 6-{3-[4-(2,3-Dimethylphenyl)-1-piperazinyl]propoxy-}-2H-1,4-benzoazine-3(4H)-one or a salt thereof in an amount effective for said treatment.

15. A method for treating hypoxia which comprises administering to a host in need thereof a 7-{3-[4-(4-Chlorophenyl)-1-piperazinyl]propoxy}-3,4-dihydrocarbostyril or a salt thereof in an amount effective for said treatment.

* * * * *

UNITED STATES PATENT AND TRADEMARK OFFICE
CERTIFICATE OF CORRECTION

PATENT NO. : 4,914,094

DATED : April 3, 1990

INVENTOR(S) : YASUO OSHIRO et al.

It is certified that error appears in the above-identified patent and that said Letters Patent is hereby corrected as shown below:

In The Claims:

Claim 4, column 15, line 33, replace "as" with --as $\equiv$ --.

Signed and Sealed this

Fourteenth Day of January, 1992

Attest:

HARRY F. MANBECK, JR.

Attesting Officer      Commissioner of Patents and Trademarks